United States Patent [19]

Gattner et al.

[11] Patent Number: 5,125,953
[45] Date of Patent: Jun. 30, 1992

[54] USE OF A MICROBICIDAL AGENT FOR THE TREATMENT OF CONCRETE ROOF TILES

[75] Inventors: Hans Gattner, Bad Nenndorf; Wolfgang Lindner, Seelze; Erich Taschenbrecker, Wunstorf; Karl Wagner, Seelze; Gerhard Wöhner, Wunstorf, all of Fed. Rep. of Germany

[73] Assignee: Riedel-De Haen Aktiengesellschaft, Seelze, Fed. Rep. of Germany

[21] Appl. No.: 605,265

[22] Filed: Oct. 29, 1990

[30] Foreign Application Priority Data

Jan. 29, 1990 [DE] Fed. Rep. of Germany ....... 4002471

[51] Int. Cl.$^5$ ............................................. A01N 43/68
[52] U.S. Cl. ................................. 71/67; 71/DIG. 1; 514/245; 514/395
[58] Field of Search ........................ 514/245, 395, 246; 544/180; 71/67, DIG. 1

[56] References Cited

U.S. PATENT DOCUMENTS

| | | | |
|---|---|---|---|
| 3,766,182 | 10/1973 | Köhne et al. | 260/249.8 |
| 3,978,217 | 8/1976 | Szoke et al. | 514/395 |
| 4,242,119 | 12/1980 | Berrer et al. | 71/67 |
| 4,710,220 | 12/1987 | Pischky | 71/67 |
| 4,906,648 | 3/1990 | Minami et al. | 514/395 |

FOREIGN PATENT DOCUMENTS 0380984 8/1990 European Pat. Off. .
3539118 7/1986 Fed. Rep. of Germany .
2151240 7/1985 United Kingdom .

OTHER PUBLICATIONS

Chemical Abstracts, "Marine antifouling coatings", JP 61/34078 A2 [86/34078], Feb. 18, 1986.
Chemical Abstracts 112: 236968d, Abstracting JP 01,223,188. Miyosawa et al. Sep. 6, 1989.

Primary Examiner—Allen J. Robinson
Assistant Examiner—John D. Pak
Attorney, Agent, or Firm—Connolly and Hutz

[57] ABSTRACT

The present invention relates to the use of methylthiocyclopropylamino-tert.-butylamino-1,3,5-triazine (Mctt) as a microbicidal agent for the treatment of concrete roof tiles.

4 Claims, No Drawings

USE OF A MICROBICIDAL AGENT FOR THE TREATMENT OF CONCRETE ROOF TILES

Concrete roof tiles become overgrown with algae and fungi relatively rapidly. Surfaces which are not exposed to direct sunlight and consequently are in a damp state for long periods in particular are discoloured an unsightly green to black by microorganisms after only a few months. Algae and fungi also make way for the growth of lichens and mosses, which with their roots may contribute towards damaging the surface and hence shorten the useful life of a concrete roof tile.

It is already known from German Offenlegungsschrift 3,740,779 that the growth of algae and fungi on flat roof surfaces can be prevented by addition of zinc powder to a coating. However, this process is adverse for ecological reasons, because heavy metal ions can be introduced into the environment, for example via the rainwater which runs off.

It is furthermore prior art to provide dispersions of plastics for roof coatings with a treatment against algal growth using dithiocarbamates, preferably zinc dimethyldithiocarbamate. However, the activity of zinc dimethyldithiocarbamate is not sufficient to prevent the growth of algae on roof tiles in the long term. The relatively high water-solubility and the lack of stability of dithiocarbamates are also factors against long-term protection of surfaces exposed to severe weathering. During production of coated roof tiles, the microbicides introduced moreover are exposed to high pH values and elevated temperatures, so that dithiocarbamates hydrolyze.

No environmentally compatible microbicide which can prevent roof tiles becoming overgrown with algae, lichens and mosses in the long term is known to date.

Methylthio-cyclopropylamino-tert.-butylamino-1,3,5-triazine (Mctt) is known as an algicide and is incorporated into facade paints for protection from algal attack. It is also employed as an antifouling additive in ship paints.

According to the prior art to date, microbicidal agents which are suitable for protecting facades, that is to say vertical surfaces, are not suitable for roof tiles because the pH, light, temperature and leaching resistance requirements on these are considerably higher and in some cases also of a different technical nature.

Extremely high pH values ($>13$) associated with high temperatures during hardening, at which the microbicides usually employed in facade coatings hydrolyze, thus arise in the production process of roof tiles. In contrast to facade coatings, a decidedly higher exposure to leaching due to precipitation running off occurs in roof tile coatings because of the inclined installation. Very much higher requirements are also imposed on light stability, especially UV stability, since the incident sunlight is very much more intense because of the non-vertical installation.

It is thus all the more surprising that the object of the present invention, that is to say of providing an agent which ensures effective and long-term protection of concrete roof tiles from attack by algae, fungi, lichens and mosses, is achieved by using methylthio-cyclopropylamino-tert.-butylamino-1,3,5-triazine (Mctt) as the microbicidal agent for treating concrete roof tiles.

The invention is particularly surprising inasmuch as the long-term action required cannot be predicted from the physical data of Mctt. For example, the compound, which was originally developed for plant protection, is described as degradable in the environment. It was furthermore not to be expected that Mctt survives the high pH values which occur on the concrete surfaces and the irradiation with sunlight and thus does not lose its activity over the years. For example, prometryn (2,4-bis-(isopropylamino)-6-methylthio-1,3,5-triazine), which is of analogous structure, hydrolyzes in an acid and in an alkaline medium by replacement of the methylthio group by the hydroxyl group.

Mctt can be used by itself or, preferably, as a mixture with one or more fungicides. Mixtures with fungicides have a preferred weight ratio of Mctt: fungicide of 1:0.1 to 1:20. A weight ratio of Mctt:fungicide of 1:0.5 to 1:5 is particularly preferred.

Preferred fungicides are fungicides which are resistant to alkali and leaching. Examples of particularly preferred fungicides are benzimidazole derivatives, such as, for example, thiabenzazole or benzimidazolyl methylcarbamate, triazole derivatives, such as, for example, propiconazole or tebuconazole, and morpholine derivatives, such as, for example, fenpropimorph. Benzimidazolyl methylcarbamate (BCM) is especially preferred.

Mctt and the fungicides mentioned are known. They can be obtained commercially or can be prepared by methods which are known to the expert.

The Mctt used according to the invention, or its mixtures with fungicides, is preferably formulated as a powder, solution or aqueous paste. Such formulations have an active compound content of 1 to 99% by weight, preferably 10 to 80% by weight, the particular remaining constituent consisting of customary formulation auxiliaries, such as, for example, dispersing agents, solvents, anticaking agents, thickeners, fillers or carriers. Solutions contain as solvents, for example, glycols or ethers or esters thereof, such as, for example, ethylene glycol, diethylene glycol or polyethylene glycol or mono- or dialkyl ethers thereof, propylene glycol, dipropylene glycol or polypropylene glycol or mono- or dialkyl ethers thereof or the correspondingly lower alkyl esters, wherein alkyl in each case denotes methyl, ethyl, n-propyl, iso-propyl or butyl.

Monoalkyl ethers of mono-, di- or triethylene glycol or mono-, di- or tripropylene glycol and esters of monoalkylglycols and polyglycols are preferred.

Butylglycol, methyldiglycol, butyldiglycol, butylglycol acetate, butyldiglycol acetate and polyethylene glycol (molecular weight 300 to 600) are particularly preferred.

The glycols mentioned can of course also be employed as mixtures with one another.

The formulations mentioned are prepared by the customary methods known to the expert. Mixtures of Mctt and fungicides are preferably prepared by mixing the un-ground fungicide, as a grinding auxiliary, with the crude, coarsely crystalline Mctt and grinding both constituents together to particle sizes of less than 40 μm in a cross-beater mill, for example a commercially available inclined-line turbo mill. The pulverulent mixture thus obtained can be converted into solutions or aqueous, pasty formulations by customary processes.

The formulations mentioned can be employed directly for the treatment of concrete roof tiles. However, they are preferably added to film-forming dispersions of plastics or coating agents containing film-forming dispersions of plastics, the coating agents finished in this manner being applied to the concrete surfaces. In addition to the film-forming polymer dispersions, the coating agents can contain further additives which are known per se to the expert, such as, for example, colour pigments (for example iron oxides and the like), solvents, plasticizers, UV absorbers, thixotropic agents (for example cellulose derivatives), fillers, adhesion promoters and the like.

The known commercial products can be employed, for example, as film-forming dispersions of plastics.

Polymer dispersions based on polyacrylate and based on styrene acrylate are preferred.

The polymer dispersions contain the active compounds in amounts of 0.01 to 5% of Mctt and 0.05 to 10% of a fungicide, preferably 0.05 to 1% of Mctt and 0.1 to 2% of the fungicide.

The formulations, the film-forming polymer dispersions and the coating agents containing film-forming polymer dispersions are used in amounts such that 0.01 to 5 g, preferably 0.05 to 2 g, of Mctt and 0.1 to 2 g of fungicide are applied per $m^2$ of concrete surface.

The use according to the invention enables concrete roof tiles to be protected in the long term from becoming overgrown with algae, fungi, lichens and mosses after only a single treatment. It is furthermore possible to restore concrete surfaces which are already overgrown and to protect them in the long term from renewed growth.

A roof freed from algae, fungi and lichens thus remained completely free from renewed growth, even after more than 2.5 years, after application of a film of plastic containing the agent according to the claims, whereas the non-treated comparison surface was completely overgrown again after this time.

EXAMPLE 1

Preparation of an Mctt-BCM formulation 500 kg of BCM and 500 kg of industrial Mctt are premixed in a forced mixer and ground to a particle size of less than 40 μm in an inclined-line turbo mill. 40 kg of carboxymethylcellulose are stirred in 2000 l of water in a dissolver until the cellulose has swollen completely. 1000 kg of the ground BCM-Mctt mixture and 1000 kg of kaolin are then stirred in until a homogeneous paste exists.

This formulation can be incorporated into aqueous concrete coating systems by the customary method, without a roughening of the surface of the resultant coating product.

EXAMPLE 2

Laboratory testing of the activity of Mctt-fungicide mixtures on alkaline concrete substrates The active compound formulations to be tested are mixed in graduated concentrations into a commercially available emulsion paint.

Biological testing is carried out on circular filter paper (No. 597 from Schleicher & Schüll, diameter 5.5 cm). For this, the filters are brushed on one side with the modified emulsion paint to be tested.

In parallel with this, fresh concrete is prepared by mixing 71.6% of screed sand (about 1.6% moisture content), 18.9% of Portland cement according to DIN 1164 and 9.5% of tapwater and is introduced into a Petri dish, the surface being smoothed with a spatula. The concrete is compacted by carefully tapping on the Petri dish several times.

The freshly coated paper filters are immediately placed on the freshly prepared moist concrete and pressed on with the aid of a spatula. The Petri dish is sealed with the aid of adhesive tape (for example Tesa tape) to prevent drying out.

The test specimens are now kept in a heating cabinet at 60° C. for 48 hours. They are then allowed to cool to room temperature and the moist filters are subsequently carefully lifted off from the concrete surface using a spatula. The filters are dried on filter paper in air for 16 hours.

The test specimens are then watered with tap water for 48 hours (series b) in the table) or 96 hours (series c) in the table, 63 l of water being used per $m^2$, in order to simulate exposure to leaching by raining. The leaching water is changed after every 24 hours.

The test for resistance to becoming overgrown by algae is carried out on solid nutrient media which are prepared as follows. 10 g of pulverulent agar, 1.00 g of calcium nitrate 4-hydrate, 0.25 g of potassium hydrogen phosphate, 0.25 g of magnesium sulphate 7-hydrate, 0.25 g of potassium chloride and 1 mg of iron(III) chloride 6-hydrate are stirred into 1 l of distilled water and the solution is sterilized in an autoclave at 121° C. for 15 minutes.

The still-liquid, hot nutrient medium is then poured in 18 ml portions into sterile Petri dishes of plastic with the aid of a sterile measuring cylinder. After solidification, the nutrient media are ready for the test.

In addition to the pre-exposed test coatings, unexposed test coatings which have been produced from the same modified emulsion paints on paper filters and have been dried are used for the biological testing. (Series a) in the table)

The untreated emulsion paint is also tested as the growth control (sample 5)).

Before infection with the algae, the dried test specimens are sterilized on each side for in each case 1 hour under UV light and placed individually with the coated side upwards on the algae nutrient agar plates under sterile conditions.

Infection is then carried out with in each case 4.5 ml of green algae culture having a cell concentration of $10^5$ to $10^6$ per ml.

The experiment is carried out in a room with diffuse light at 16°-20° C. To promote faster growth of the green algae, the specimens are illuminated overnight using incandescent bulbs.

After 14 days, the paint films are evaluated in accordance with the following scheme:

0 paint film not overgrown
1 paint film slightly overgrown, less than 10%
2 paint film overgrown, less than 30%
3 paint film significantly overgrown, less than 60%
4 paint film heavily overgrown, more than 60%

| Designation of the samples | Paint film weight g/$m^2$ | Exposure | Evaluation of growth of algae | |
|---|---|---|---|---|
| | | | Chlorella fusca | Algae in practice |
| 1.) Paint containing 0.1% of Mctt and 0.1% of BCM | 106 | a) b) c) | 0 0 0 | 0 0 0 |
| 2.) Paint containing 0.2% of Mctt and 0.2% of BCM | 139 | a) b) c) | 0 0 0 | 0 0 0 |
| 3.) Paint containing 0.1% of Mctt and 0.2% of BCM | 118 | a) b) c) | 0 0 0 | 0 0 0 |
| 4.) Comparison example | 117 | a) | 0 | 0 |

-continued

| Designation of the samples | Paint film weight g/m² | Ex- posure | Evaluation of growth of algae | |
|---|---|---|---|---|
| | | | Chlorella fusca | Algae in practice |
| Paint containing | | b) | 2 | 3 |
| 0.5% of zinc dimethyl- | | c) | 4 | 4 |
| dithiocarbamate and | | | | |
| 0.1% of BCM | | | | |
| 5.) Growth control | 120 | a) | 4 | 4 |
| Paint without additive | | b) | 4 | 4 |
| | | c) | 4 | 4 |

Mctt: methylthio-cyclopropylamino-tert.-butylamino-1,3,5-triazine
BCM: benzimidazolyl methylcarbamate
Exposure:
a) No exposure
b) Test specimens placed on freshly prepared roof tile cement at 60° C. for 48 hours, subsequent watering for 48 hours
c) Test specimens placed on freshly prepared roof tile cement at 60° C. for 48 hours, subsequent watering for 96 hours The example shows that the microbicides according to the claims completely prevent the growth of algae on the coating of plastic even after exposure to high pH values, temperatures and watering, whereas a treatment which corresponds to the prior art does not survive exposures similar to those in practice and remains inadequately active.

EXAMPLE 3

Cleaning of a roof overgrown with mosses, lichens, fungi and algae

The long-term effectiveness of a preservative system for concrete roof tiles under conditions in practice is determined by this experiment. The building is a single-storey one-family house in the rural heavy rainfall environment in Northern Germany. The house is surrounded by a green area about 30×30 m² in size, on which were growing individual trees and bushes, mainly juniper, birch, spruce and pine, so that growth conditions for algae and fungi were the optimum.

The west north-west side of the roof most heavily affected by algae, mosses and lichens was taken into consideration. The entire experimental area was 12×17 roof tiles, which were divided into 3 sectors. The restored experimental sectors were thus 4×17 roof tiles in size (6.8 m²).

The roof was heavily overgrown with algae, mosses and lichens. It was moreover contaminated with mechanical dirt. The previously red concrete roof tiles were therefore almost black, and otherwise discoloured green by areas of algal growth.

The dirt and growth lying on all three sectors was removed by mechanical hydraulic cleaning using a high pressure jet apparatus.

Sector 1 was provided with a coating according to the claims as follows.

20 g of Mctt were dissolved in 40 g of butyldiglycol and stirred, together with 10 g of ground BCM, into 600 g of polyacrylate dispersion (Mowilith ® DM 771—Hoechst AG, Frankfurt). This mixture was stirred into 1340 g of water. 947 g of the dispersion thus obtained was applied directly onto the area to be cleaned using a garden spray. Starting at the ridge, the preservative solution was sprayed onto the roof surface so that as far as possible the whole area, including the edges of the roof tiles, was wetted. The underneath edges of the roof tiles were preferably sprayed in a second operation.

After about 25 minutes, the tile had dried off on the surface. 1.39 g of Mctt per m² were applied to the roof in this way.

As a growth control, the second sector, of the same size, was sprayed with a solution of 5 g of sodium dichloroisocyanurate, 5 g of Dodigen ® 2815 (Hoechst AG, Frankfurt) and 12 g of sodium benzoate in 1200 g of water, after the same mechanical cleaning, and coated as described above with a polymer dispersion which had not been given a microbicidal treatment.

As a comparison, which represents the current prior art, the third experimental sector was coated, after mechanical cleaning, with a polymer dispersion which contained zinc dimethyldithiocarbamate, 1.3 g of zinc dimethyldithiocarbamate per m² being applied.

After 2 years, the experimental sectors were evaluated and in each case one roof tile was examined under the microscope.

No algae, fungi or lichens could be detected on sector 1, which was preserved with the agent according to the claims, even after two years, whereas sector 2 was again completely overgrown with algae and lichens and discoloured black-green. Sector 3 revealed significant deposits of algae and fungal growth especially on the underneath edges.

EXAMPLE 4

Comparison of the activity in facade paints and in roof tile coatings

The active compound formulations to be tested are mixed in graduated concentrations into a commercially available emulsion paint.

For testing the usability of the agent according to the claims in roof tile coatings, test specimens are produced as described in Example 2 and subjected to preliminary exposure as in Example 2, series c.

As a comparison, the conditions to which a facade paint is exposed are simulated as follows:

The freshly coated paper filters described in Example 2 are dried on filter paper in air for 16 hours.

The test specimens are then watered with tap water for 48 hours, 63 l of water per m² being employed, in order to simulate exposure to leaching by raining. The leaching water is changed after every 24 hours.

Testing of the resistance to becoming overgrown by algae is carried out as described in Example 2. The evaluation is also carried out as described in that example.

| Designation of the samples | Paint film weight g/m² | Ex- posure | Evaluation of growth of algae | |
|---|---|---|---|---|
| | | | Chlorella fusca | Algae in practice |
| 1.) Paint containing | 189 | a) | 0 | 0 |
| 0.15% of Mctt and | | b) | 0 | 0 |
| 0.05% of BCM | | c) | 0 | 0 |
| 2.) Paint containing | 173 | a) | 0 | 0 |
| 0.05% of Mctt and | | b) | 0 | 0 |
| 0.05% of BCM | | c) | 0 | 0 |
| 3.) Comparison example | 196 | a) | 0 | 0 |
| Paint containing | | b) | 4 | 4 |
| 0.2% of 2-octyliso- | | c) | 0 | 0 |
| thiazolin-3-one | | | | |
| 0.08% of BCM | | | | |
| 4.) Growth control | 206 | a) | 4 | 4 |
| Paint without additive | | b) | 4 | 4 |

-continued

| Designation of the samples | Paint film weight g/m² | Ex-posure | Evaluation of growth of algae | |
|---|---|---|---|---|
| | | | Chlorella fusca | Algae in practice |
| | | c) | 4 | 4 |

Mctt: Methylthio-cyclopropylamino-tert.-butylamino-1,3,5-triazine
BCM: benzimidazolyl methylcarbamate
Exposure:
a) No exposure
b) Test specimens placed on freshly prepared roof tile cement at 60° C. for 48 hours, subsequent watering for 96 hours (corresponds to the exposure for the roof tile)
c) Watering for 48 hours (comparison exposure for a facade paint)

The example shows that the agents according to the claims are still completely active when used in roof tile coatings even under the higher degrees of exposure, whereas although the agents of the prior art are still active in facade paints, they are no longer so in roof tile coatings.

We claim:

1. A method for the microbicidal treatment of concrete roof tiles comprising applying a microbicidally effective amount of a mixture of methylthiocyclopropylamino-tert.-butylamino-1,3,5-triazine (Mctt) and benzimidazolyl methylcarbamate as a microbicidal agent to the concrete roof tiles.

2. A method according to claim 1 wherein the weight ratio of Mctt:benzimidazoyl methylcarbamate is 1:0.1 to 1:20.

3. A method according to claim 1 wherein the weight ratio of Mctt:benzimidazolyl methylcarbamate is 1:0.5 to 1:5.

4. A method according to claim 1 wherein the mixture of Mctt and benzimidazolyl methylcarbamate is combined with a film-forming polyacrylate or acrylate dispersion.

* * * * *